United States Patent [19]
Coburn et al.

[11] Patent Number: 6,087,373
[45] Date of Patent: Jul. 11, 2000

[54] THROMBIN INHIBITORS

[75] Inventors: Craig Coburn, Skippack; Joseph P. Vacca, Telford; Peter D. Williams, Harleysville, all of Pa.

[73] Assignee: Merck & Co., Inc., Rahway, N.J.

[21] Appl. No.: 09/157,964

[22] Filed: Sep. 21, 1998

Related U.S. Application Data

[60] Provisional application No. 60/059,801, Sep. 23, 1997.

[51] Int. Cl.$^7$ .......................... A61K 31/4375; A61P 9/10; C07D 471/04
[52] U.S. Cl. ............................................ 514/300; 546/122
[58] Field of Search .............................. 546/122; 514/300

[56] References Cited

U.S. PATENT DOCUMENTS

| | | |
|---|---|---|
| 4,296,114 | 10/1981 | Appleton et al. . |
| 5,260,307 | 11/1993 | Ackermann et al. . |
| 5,272,158 | 12/1993 | Hartman et al. . |
| 5,405,854 | 4/1995 | Ackermann et al. . |
| 5,459,142 | 10/1995 | Tone et al. . |
| 5,510,369 | 4/1996 | Lumma et al. . |
| 5,585,385 | 12/1996 | Natsugari et al. ........................ 514/300 |
| 5,602,253 | 2/1997 | Antonsson et al. . |

FOREIGN PATENT DOCUMENTS

| | | |
|---|---|---|
| 0 262 096 | 3/1988 | European Pat. Off. . |
| 0 509 769 A2 | 10/1992 | European Pat. Off. . |
| 0 648 780 A1 | 4/1995 | European Pat. Off. . |
| WO94/25051 | 11/1994 | WIPO . |
| 96/11697 | 4/1996 | WIPO . |
| 96/31504 | 10/1996 | WIPO . |
| 96/32110 | 10/1996 | WIPO . |
| 97/01338 | 1/1997 | WIPO . |
| WO 98/17274 | 4/1998 | WIPO . |

OTHER PUBLICATIONS

Semple et al., J. Med. Chem., vol. 39 (1996), pp. 4531–4536, "Design, synthesis, and evolution of a novel, selective, and orally bioavailable class of thrombin inhibitors . . . ".

Bernstein, et al., J. Med. Chem., 37, 3313–3326 "Nonpeptidic Inhibitors of Human Leukocyte Elastase . . . ", 1994.

Temple, Carroll, Jr. and Gregory A. Rener, J. Med. Chem., "Antimitotic Agents: Ring Analogues and Derivatives of Ethyl . . . ", vol. 35, pp. 4809–4812 (1992).

Mack, Helmut et al., J. Enzyme Inhibition, "Design, Synthesis and Biological activity of Novel Rigid . . . , " vol. 9, pp. 73–86 (1995).

Edwards, Philip D. et al., J. American Chemical Soc., "Design, Syntheses, and Kinetic Evaluation of a Unique Class of Elastase Inhibitors . . . , " vol. 114, pp. 1854–1863 (1992).

Brown, Frederick J. et al., J. Med. Chem., "Design of Orally Active, Non–Peptidic Inhibitors of Human Leukocyte Elastase," vol. 37, pp. 1259–1261 (1994).

*Primary Examiner*—Patricia L. Morris
*Attorney, Agent, or Firm*—Richard S. Parr; Melvin Winokur

[57] ABSTRACT

A compound which inhibits human thrombin and which has the general structure

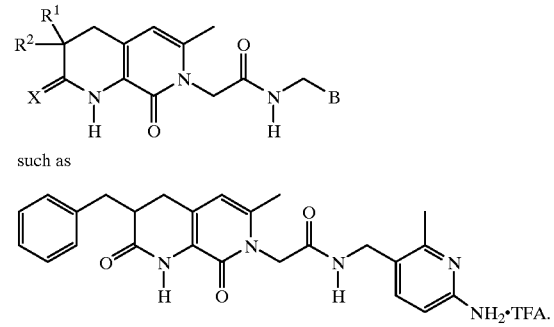

such as 6 Claims, No Drawings

THROMBIN INHIBITORS

This is a non-provisional application of provisional application Ser. No. 60/059,801, filed Sep. 23, 1997.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives. Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoiminomethyl)amino]butyl]-1-[N-(2-naphthalenylsulfonyl)-L-phenylalanyl]-L-prolinamide.

WO 94/29336 describes compounds which are useful as thrombin inhibitors.

SUMMARY OF THE INVENTION

A compound which inhibits human thrombin and which has the general structure

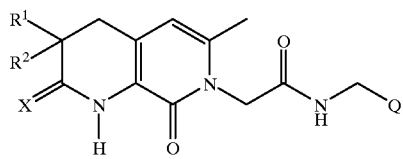

such as

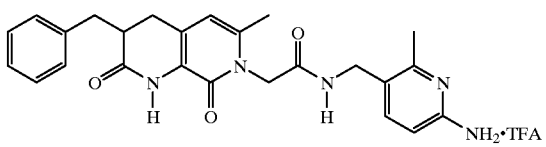

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes the use of a compound of the invention in the manufacture of a medicament for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal.

The invention also includes a method for reducing the thrombogenicity of a surface in a mammal by attaching to the surface, either covalently or noncovalently, a compound of the invention.

DETAILED DESCRIPTION OF THE INVENTION

Compounds of the invention have the following structure:

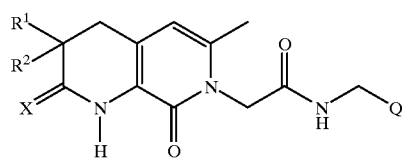

wherein
X is O or $H_2$;
$R^1$ and $R^2$ are independently selected from the group consisting of
  hydrogen,
  $C_{1-6}$ alkyl-,
  $C_{2-6}$ alkenyl,
  $C_{2-6}$ alkynyl,
  $C_{3-8}$ cycloalkyl-
  $C_{3-8}$cycloalkyl $C_{1-6}$alkyl-,
  di($C_{3-8}$cycloalkyl) $C_{1-6}$alkyl-,
  aryl,
  aryl $C_{1-6}$ alkyl-,
  di(aryl) $C_{1-6}$ alkyl-,
    wherein aryl is an unsaturated 6-carbon ring, either unsubstituted or substituted with —OH, —$NH_2$, $C_{1-6}$alkyl, $C_{3-8}$cycloalkyl, or halogen;
and
Q is

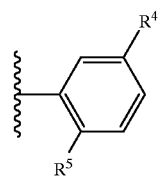

wherein $R^4$ and $R^5$ are independently selected from the group consisting of
  hydrogen,
  $C_{1-4}$ alkyl, $C_{2-4}$ alkenyl,
$C_{2-4}$ alkynyl,
$C_{1-4}$ alkoxy,
halogen,
—COOH,
—OH,
—COOR$^7$, where R$^7$ is $C_{1-4}$alkyl,
—CONR$^8$R$^9$, where R$^8$ and R$^9$ are independently hydrogen or $C_{1-4}$alkyl,
—OCH$_2$CO$_2$H,
—OCH$_2$CO$_2$CH$_3$,
—OCH$_2$CO$_2$(CH$_2$)$_{1-3}$CH$_3$,
—O(CH$_2$)$_{1-3}$C(O)NR$^{10}$R$^{11}$, wherein R$^{10}$ and R$^{11}$ are independently hydrogen, $C_{1-4}$alkyl, $C_{3-7}$ cycloalkyl, or —CH$_2$CF$_3$,
—(CH$_2$)$_{1-4}$OH,
—NHC(O)CH$_3$,
—NHC(O)CF$_3$,
—NHSO$_2$CH$_3$,
—SO$_2$NH$_2$;
or Q is

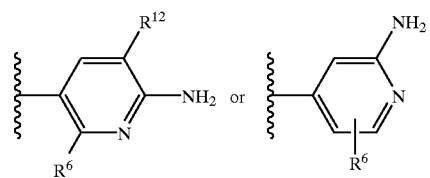

wherein R$^6$ and R$^{12}$, same or different, are
hydrogen,
$C_{1-6}$ alkyl-,
$C_{2-6}$ alkenyl-,
$C_{2-6}$ alkynyl,
$C_{3-8}$ cycloalkyl-,
aryl,
aryl $C_{1-6}$alkyl-
wherein aryl is an unsaturated 6-carbon ring either unsubstituted or substituted with —OH, —NH$_2$, $C_{1-6}$alkyl, $C_{3-8}$ cycloalkyl, or halogen.
and pharmaceutically acceptable salts thereof.

A class of these compounds is

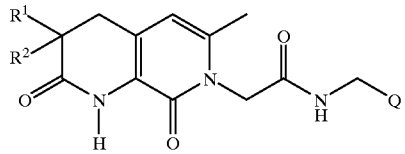

wherein
R$^1$ and R$^2$ are independently selected from the group consisting of:
hydrogen,
$C_{1-6}$alkyl,
$C_{3-8}$cycloalkyl$C_{1-6}$alkyl-,
di($C_{3-8}$cycloalkyl)$C_{1-6}$alkyl-,
aryl $C_{1-6}$alkyl-,
di(aryl) $C_{1-6}$alkyl-,
wherein aryl is unsubstituted, monosubstituted or disubstituted with halogen,
and Q is

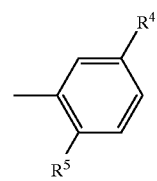

wherein R$^4$ and R$^5$ are independently selected from the group consisting of
hydrogen,
halogen, or
—OCH$_2$C(O)NHR$^{11}$, wherein R$^{11}$ is $C_{1-4}$ alkyl,
or Q is

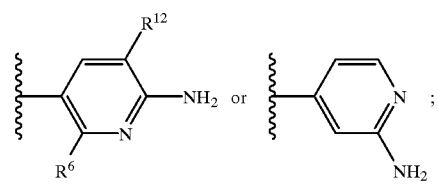

where R$^6$ and R$^{12}$, same or different, are hydrogen or —CH$_3$, and pharmaceutically acceptable salts thereof.

A group of this class of compounds is

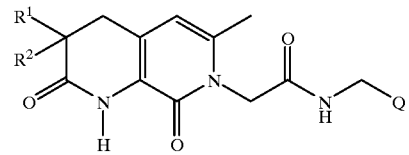

wherein

R$^1$ is hydrogen,

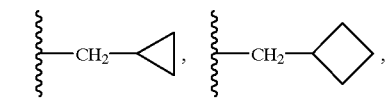

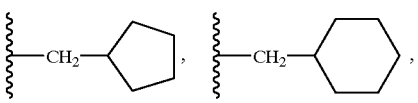

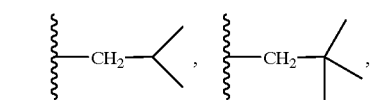

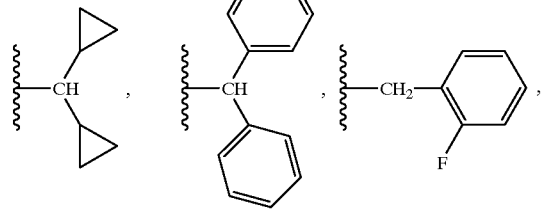

-continued

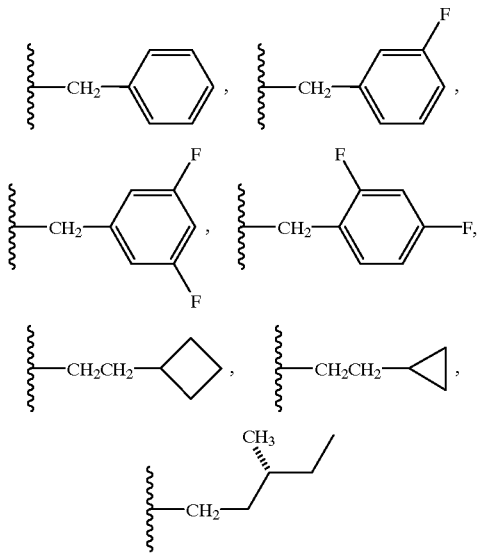

$R^2$ is hydrogen, $CH_3$, $C_{1-6}$ alkyl, and aryl$C_{1-6}$alkyl; and Q is

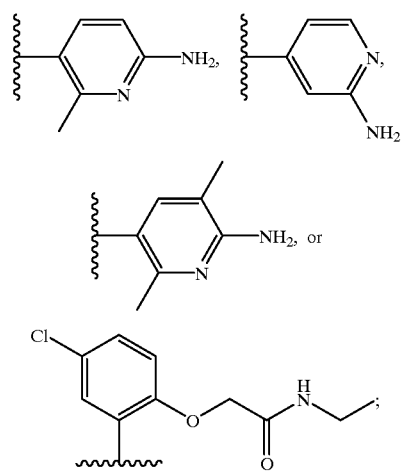

and pharmaceutically acceptable salts thereof.
A subgroup of this group of compounds is

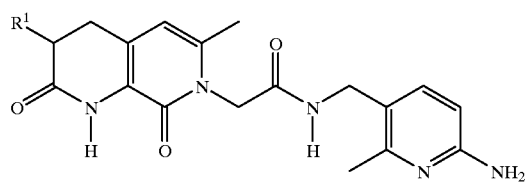

wherein
$R^1$ is hydrogen,

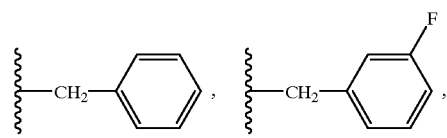

-continued

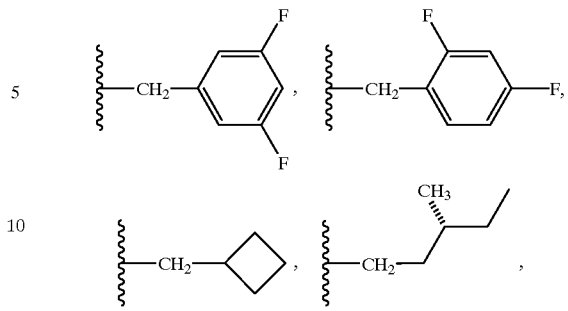

and pharmaceutically acceptable salts thereof.

Specific exemplifications of this class are shown in the table below:

TABLE 1

| R1 | R2 | Q | Ki (nM) |
|---|---|---|---|
| H | H | 2-methyl-5-(6-aminopyridyl) | 350 |
| benzyl | H | 2-methyl-5-(6-aminopyridyl) | 0.75 |
| (S)-benzyl | H | 2-methyl-5-(6-aminopyridyl) | 0.36 |
| (R)-benzyl | H | 2-methyl-5-(6-aminopyridyl) | 12 |
| 3-fluorobenzyl | H | 2-methyl-5-(6-aminopyridyl) | 1.1 |

TABLE 1-continued

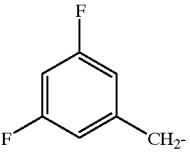

| R1 | R2 | Q | Ki (nM) |
|---|---|---|---|
| 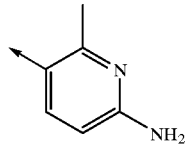 | H | 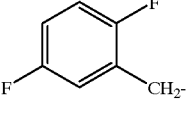 | 1.5 |
| 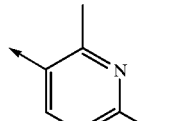 | H | 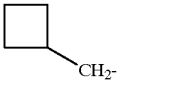 | 0.64 |
| 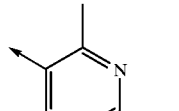 | H | 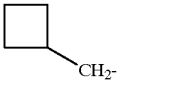 | 0.16 |
| 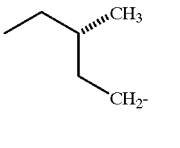 | H | 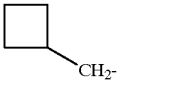 | 0.52 |

Exemplifications also include the pharmaceutically acceptable salts of the above-identified compounds.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| Ph | phenyl |
| Bn | benzyl |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| Other | |
| (BOC)$_2$O (BOC$_2$O) | di-t-butyl dicarbonate |

| ABBREVIATIONS | |
|---|---|
| n-Bu$_4$N+F– | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | diinethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| Amino Acid | |
| Ile | Isoleucine |
| Phe | Phenylalanine |
| Pro | Proline |
| Ala | Alanine |
| Val | Valine |

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

As used herein, except where noted, "alkyl" is intended to include both branched- and straight-chain saturated aliphatic hydrocarbon groups having, unless otherwise noted, 1–8 carbon atoms (Me is methyl, Et is ethyl, Pr is propyl, Bu is butyl). "Alkenyl" is intended to include both branched- and straight-chain unsaturated aliphatic hydrocarbon groups having, unless otherwise noted, 1–8 carbon atoms, e.g. ethenyl, propenyl, etc. "Cycloalkyl" includes cyclic saturated aliphatic hydrocarbon groups having 3–8 carbon atoms (e.g. "C$_{3-8}$cycloalkyl" is intended to include cyclopropyl, cyclobutyl, cyclopentyl, cyclohexyl and cycloheptyl, and the like). The term "C$_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like. The term "aryl" as used herein except where noted, represents a stable 6- to 10-membered mono- or bicyclic ring system such as phenyl, or naphthyl. The aryl ring can be unsubstituted or substituted with one or more of C$_{1-4}$ lower alkyl; hydroxy; alkoxy; halogen; amino. "Alkoxy" represents an alkyl group having 1–8 carbon atoms attached through an oxygen bridge. "Halo", as used herein, means fluoro, chloro, bromo and iodo. "Counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

Under standard nomenclature used throughout this disclosure unless specified otherwise, the terminal portion of the designated side chain is described first followed by the adjacent functionality toward the point of attachment. For example, an ethyl substituent substituted with "methylcarbonylamino" is equivalent to

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prothesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems. For example, compounds of the invention may be used to coat a stent in order to inhibit local coagulation which frequently occurs with stent implantation.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is elected in accordance with a variety of factors including type, species, ge, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specified otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical tablet cores suitable for administration of thrombin inhibitors are comprised of, but not limited to, the following amounts of standard ingredients:

| Suggested Ranges of Composition for Excipients in Uncoated Tablet Cores | | | |
| --- | --- | --- | --- |
| Excipient | General Range (%) | Preferred Range (%) | Most Preferred Range (%) |
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, heparin or warfarin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin or simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The following examples are illustrative of the invention as contemplated by the inventors and should not be construed as being limits on the scope or spirit of the instant invention.

Amide couplings used to form the compounds of this invention are typically performed by the carbodiimide method with reagents such as dicyclohexylcarbodiimide, or 1-ethyl-3-(3-dimethylaminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

Compounds of the invention can be prepared, for example, using starting materials, intermediates, and general procedures outlined below.

Preparation of Starting Materials:

4-Formyl-2-Methoxy-6-Methyl-3-Nitropyridine

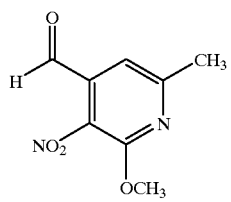

Step A: Ethyl 6-methyl-3-nitropyridone 4-carboxylate

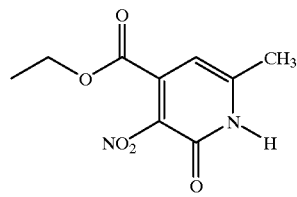

To a slurry nitroacetamide ammonia salt (70.3 g, 581 mmol) in 400 mL of deionized water was added 100 g (633 mmol, 1.09 equiv.) of ethyl 2,4-dioxovalerate followed by a solution of piperdinium acetate (prepared by adding 36 mL of piperdine to 21 mL of acetic acid in 100 mL of water). The resulting solution was stirred at 40° C. for 16 h then cooled in an ice bath. The precipitated product was filtered and washed with 50 mL of cold water to afford the above pyridone as a yellow solid.

$^1$H NMR (CDCl$_3$) d 6.43 (s, 1H), 4.35 (q, J=7 Hz, 2H), 2.40 (s, 3H), 1.35 (t, J=7 Hz, 3H).

Step B: Ethyl 2-methoxy-6-methyl-3-nitropyridine 4-carboxylate

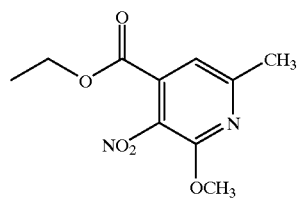

A solution of the pyridone from step A (6.2 g, 27.4 mmol) in 50 mL of DCM was treated with 4.47 g (30.2 mmol) of solid trimethyloxonium tetrafluoroborate and the mixture was stirred at 40° C. until the reaction was judged to be complete by HPLC (typically 24–72 h). The reaction mixture was concentrated to one-third volume, loaded onto a silica gel column and eluted with 2:3 EtOAc/Hexane to afford the methoxy pyridine as a yellow liquid.

$^1$H NMR (CDCl$_3$) d 7.2 (s, 1H), 4.35 (q, J=7 Hz, 2H), 4.05 (s, 3H), 2.55 (s, 3H), 1.35 (t, J=7 Hz, 3H).

Step C: 4-Hydroxymethyl-2-methoxy-6-methyl-3-nitropyridine

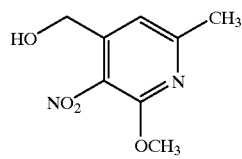

To a −70° C. solution of ester from step B (5.4 g, 22.5 mmol) in 140 mL of DCM was added 56.2 mL (56.2 mmol) of DIBAL-H (IM in hexane) by dropping funnel. The resulting solution was stirred for 1 h then warmed to room temperature over an additional hour. The reaction mixture was quenched by the careful addition of saturated NaK tartrate. Stirring was continued for 30 min then the solid was filtered and washed with 100 mL of DCM. The filtrate was extracted with 2×50 mL of saturated NaK tartrate then brine (25 mL). The yellow solution was concentrated and chromatographed (2:3 EtOAc/Hexane) to afford the desired alcohol as a yellow solid.

$^1$H NMR (CDCl$_3$) d 7.00 (s, 1H), 4.70 (s, 2H), 4.05 (s, 3H), 2.50 (s, 3H), 2.10 (bs, 1H).

Step D: 4-Formyl-2-methoxy-6-methyl-3-nitropyridine

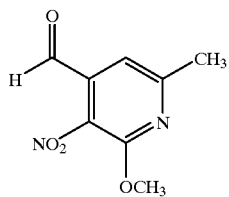

To a −70° C. solution of oxalyl chloride (2.0 mL, 22 mmol) in 50 mL of DCM was added 3.4 mL (44 mmol) of DMSO in 10 mL of DCM by dropping funnel. After 2 min, the reaction mixture was treated with 3.99 g (20 mmol) of the alcohol from step C in 20 mL of DCM. The solution was stirred for an additional 15 min at −70° C., treated with 14 mL (50 mmol) of Et$_3$N and warmed to ambient temperature over 90 min. The reaction was quenched with 100 mL of water and the two phases were separated. The aqueous phase was extracted with 100 mL of DCM and the combined organic extracts were washed with 50 mL of brine and dried over MgSO$_4$. The yellow solution was concentrated and chromatographed (2:3 EtOAc/Hexane) to afford the aldehyde as a yellow solid.

$^1$H NMR (CDCl$_3$) d 10.05 (s, 1H), 7.10 (s, 1H), 4.70 (s, 2H), 4.05 (s, 3H), 2.60 (s, 3H).

General procedure for the synthesis of intermediate phosphonates:

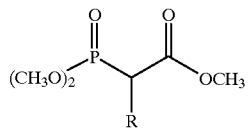

Intermediate 1 (I-1): Trimethyl 2-benzyl-2-phosphonoacetate (R=PhCH$_2$—):

To a slurry of 400 mg (16.7 mnol) of NaH in 12 mL of DMSO was added neat trimethyl phosphonoacetate (2.4 mL, 14.9 mmol). The reaction mixture was stirred for 20 min then treated with 1.4 mL (11.9 mmol) of benzyl bromide and stirring was continued for 16 h. The homogeneous solution was diluted with 25 mL of ether and washed with 6×10 mL of water then brine. The solution was dried (MgSO$_4$), concentrated and chromatographed (4:1 EtOAc/Hexane) to afford the title compound as a colorless liquid.

$^1$H NMR (CDCl$_3$) d 7.25 (m, 5H), 3.85 (s, 3H), 3.80 (s, 3H), 3.65 (s, 3H), 3.25 (m, 3H).

Intermediate 2 (I-2): Trimethyl 2-cyclobutyl-2-phosphonopropionate (R=c—BuCH$_2$—):

To a slurry of 2.0 g (80.0 mmol) of NaH in 12 mL of DMSO was added neat trimethyl phosphonoacetate (12.6 mL, 69.2 mmol). The reaction mixture was stirred for 20 min then treated with 7.9 mL (53.3 mmol) of (bromomethyl) cyclobutane and stirring was continued for 16 h. The homogeneous solution was diluted with 100 mL of ether, quenched to pH=7 with 0.25 N HCl and washed with 6×10 mL of water then brine. The solution was dried (MgSO$_4$), concentrated and chromatographed (4:1 EtOAc/Hexane) to afford the title compound as a colorless liquid.

$^1$H NMR (CDCl$_3$) d 3.85 (s, 3H), 3.80 (s, 3H), 3.65 (s, 3H), 2.90 (m, 1H), 2.4–1.6 (m, 9H).

Intermediate 3 (1–3): Trimethyl 2-cyclopropyl-2-phosphonopropionate (R=c—PrCH$_2$—):

To a slurry of 400 mg (16.7 mmol) of NaH in 12 mL of DMSO was added neat trimethyl phosphonoacetate (2.4 mL, 14.9 mmol). The reaction mixture was stirred for 20 min then treated with 1.2 mL (11.9 mmol) of (bromomethyl) cyclopropane and stirring was continued for 16 h. The homogeneous solution was diluted with 100 mL of ether, quenched to pH=7 with 0.25 N HCl and washed with 6×10 mL of water then brine. The solution was dried (MgSO$_4$), concentrated and chromatographed (4:1 EtOAc/Hexane) to afford the title compound as a colorless liquid.

$^1$H NMR (CDCl$_3$) d 3.85 (s, 3H), 3.80 (s, 3H), 3.78 (s, 3H), 3.10 (m, 1H), 2.0 (m, 1H), 1.70 (m, 1H), 0.75 (m, 1H), 0.4 (m, 2H), 0.10 (m, 2H).

Intermediate 4 (I-4): Trimethyl 2-(2-Fluorobenzyl)-2-phosphonoacetate (R=2—F—Bn—):

To a slurry of 400 mg (16.7 mmol) of NaH in 12 mL of DMSO was added neat trimethyl phosphonoacetate (2.4 mL, 14.9 mmol). The reaction mixture was stirred for 30 min then treated with 1.44 mL (11.9 mmol) of 2-fluorobenzyl bromide and stirring was continued for 16 h. The homogeneous solution was diluted with 100 mL of ether, quenched to pH=7 with 0.25 N HCl and washed with 6×10 mL of water then brine. The solution was dried (MgSO$_4$), concentrated and chromatographed (4:1 EtOAc/Hexane) to afford the title compound as a colorless liquid.

$^1$H NMR (CDCl$_3$) d 7.4–7.0 (m, 4H), 3.85 (s, 3H), 3.80 (s, 3H), 3.65 (s, 3H), 3.4–3.2 (m, 3H).

Intermediate 5 (I-5): Trimethyl 2-(3-Fluorobenzyl)-2-phosphonoacetate (R=3—F—Bn—):

To a slurry of 400 mg (16.7 mmol) of NaH in 12 mL of DMSO was added neat trimethyl phosphonoacetate (2.4 mL, 14.9 mmol). The reaction mixture was stirred for 30 min then treated with 1.44 mL (11.9 mmol) of 3-fluorobenzyl bromide and stirring was continued for 16 h. The homogeneous solution was diluted with 100 mL of ether, quenched to pH=7 with 0.25 N HCl and washed with 6×10 mL of water then brine. The solution was dried (MgSO$_4$), concentrated and chromatographed (4:1 EtOAc/Hexane) to afford the title compound as a colorless liquid.

$^1$H NMR (CDCl$_3$) d 7.2 (m, 1H), 6.90 (m, 3H), 3.85 (s, 3H), 3.80 (s, 3H), 3.65 (s, 3H), 3.4–3.2 (m, 3H).

Intermediate 6 (I-6): Trimethyl 4-(S)-Methyl-2-phosphonohexenoate [R=—CH$_2$CH(S)—(CH$_3$)CH$_2$CH$_3$]:

To a slurry of 200 mg (8.3 mmol) of NaH in 5 mL of DMSO was added neat trimethyl phosphonoacetate (1.1 mL, 6.9 mmol). The reaction mixture was stirred for 20 min then treated with 0.66 mL (5.1 mmol) of 1-iodo-2-(S)-methylbutane and stirring was continued for 16 h. The homogeneous solution was diluted with 20 mL of ether, quenched to pH=7 with 0.25 N HCl and washed with 6×5 mL of water then brine. The solution was dried (MgSO$_4$), concentrated and chromatographed (4:1 EtOAc/Hexane) to afford the title compound as a colorless liquid.

$^1$H NMR (CDCl$_3$) d 3.85–3.70 (6 singlets, 9H), 3.05 (m, 1H), 2.2–1.2 (m, 5H), 0.85 (m, 6H).

Intermediate 7 (I-7): Trimethyl 2-(2,5-Difluorobenzyl)-2-phosphonoacetate (R=2,5-di—F—Bn—):

To a slurry of 339 mg (14.1 mmol) of NaH in 10 mL of DMSO was added neat trimethyl phosphonoacetate (1.95 mL, 9.5 mmol). The reaction mixture was stirred for 20 min then treated with 1.24 mL (9.67 mmol) of 2,5-difluorobenzyl bromide and stirring was continued for 16 h. The homogeneous solution was diluted with 50 mL of ether, quenched to pH=7 with 0.25 N HCl and washed with 6×5 mL of water then brine. The solution was dried (MgSO$_4$), concentrated and chromatographed (4:1 EtOAc/Hexane) to afford the title compound as a colorless liquid.

$^1$H NMR (CDCl$_3$) d 6.95 (m, 3H), 3.85 (s, 3H), 3.80 (s, 3H), 3.70 (s, 3H), 3.4–3.2 (m, 3H).

Intermediate 8 (1–8): Trimethyl 2-(3,5-Difluorobenzyl)-2-phosphonoacetate (R=3,5-di—F—Bn—):

To a slurry of 169 mg (7.0 mmol) of NaH in 5 mL of DMSO was added neat trimethyl phosphonoacetate (0.97 mL, 4.75 mmol). The reaction mixture was stirred for 20 min then treated with 1.0 g (4.83 mmol) of 3,5-difluorobenzyl bromide and stirring was continued for 16 h. The homogeneous solution was diluted with 30 mL of ether, quenched to pH=7 with 0.25 N HCl and washed with 6×5 mL of water then brine. The solution was dried (MgSO$_4$), concentrated and chromatographed (EtOAc) to afford the title compound as a cololess liquid.

$^1$H NMR (CDCl$_3$) d 6.85 (m, 3H), 3.85 (s, 3H), 3.80 (s, 3H), 3.70 (s, 3H), 3.3–3.1 (m, 3H).

General procedure for making fused lactam thrombin inhibitors:

EXAMPLE 1

Preparation of

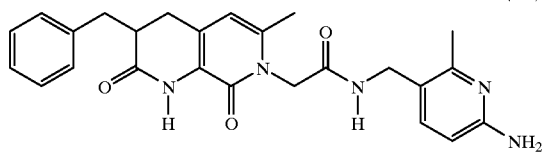

(1-7)

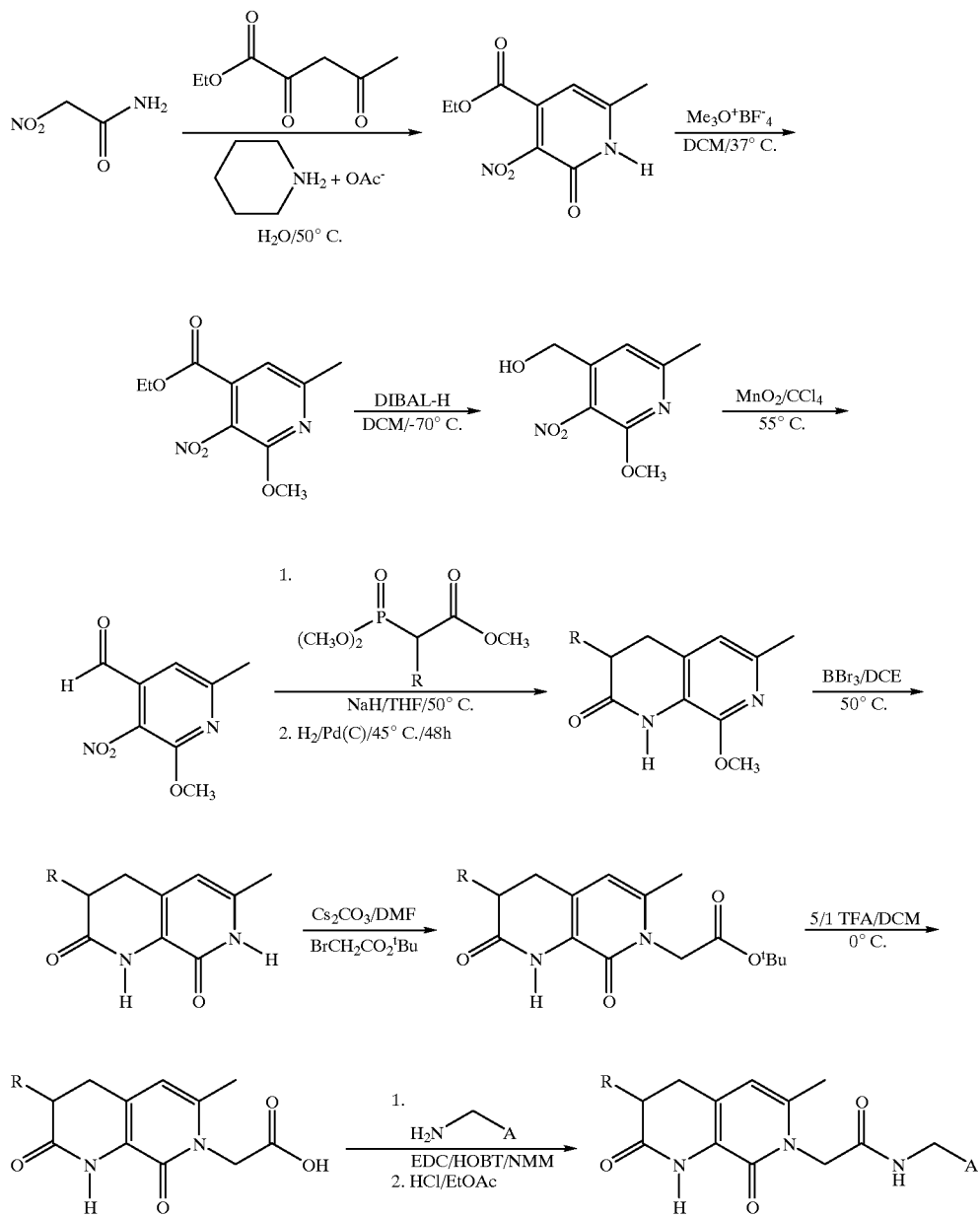

Step 1-A:

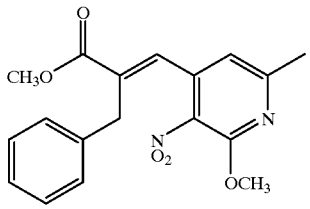
(1-1)

To a 0° C. solution of intermediate phosphonate I-1 (1.36 g, 5.0 mmol) in 25 mL of THF was added 145 mg (4.75 mmol) of NaH. The mixture was stirred for 30 min before the dropwise addition of 930 mg (4.75 mmol) of 4-formyl-2-methoxy-3-nitropyridine in 15 mL of THF. The solution was then heated at 50° C. for 3 h, cooled and evaporated. The residue was redissolved in 100 mL of EtOAc and quenched to pH=7 with saturated NH$_4$Cl. The organic phase was washed with brine and dried over MgSO$_4$. Column chromatography (2:3 EtOAc/Hexane) afforded the desired olefin as a mixture of E- and Z-isomers.

$^1$H NMR (CDCl$_3$) d 7.60 (s, 1H), 7.40–7.00 (m, 6H), 6.60 (2 singlets, 2H), 4.00 (2 singlets, 6H), 3.75 (2 singlets, 8H), 2.40 (2 singlets, 6H).

Step 1-B:

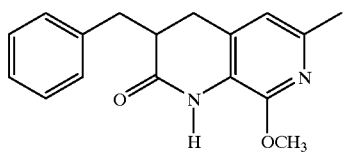
(1-2)

To a solution of nitro olefin 1—1 (1.6 g, 4.75 mmol) in 50 mL of EtOAc was added 400 mg of 10% Pd(C). Hydrogen gas was added and the solution was heated at 50° C. for 16. The reaction mixture was filtered through Celite and the filtrate evaporated. Column chromatography (2:3 EtOAc/Hexane) afforded the bicyclic lactam as a white solid.

$^1$H NMR (CDCl$_3$) d 7.45 (bs, 1H), 7.40–7.20 (m, 5H), 6.45 (s, 1H), 3.95 (s, 3H), 3.35 (dd, 1H), 2.80 (m, 2H), 2.60 (m, 2H), 2.40 (s, 3H).

Step 1-C:

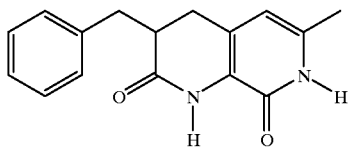
(1-3)

To a 23° C. solution of methoxypyridine 1–2 (700 mg, 2.48 mmol) in 25 mL of dichloroethane was added 8.0 mL (8.0 mmol) of BBr$_3$ (1M in DCM). An insoluble gum precipitates within 5 min and the reaction was allowed to stir an additional 90 min before quenching to pH=8 with saturated NaHCO$_3$. The mixture was diluted with 100 mL of EtOAc and 10 mL THF. The aqueous phase was discarded and the organic solution was washed with 10 mL of water then 10 mL of brine. Evaporation of the solvent left a tan colored solid which was used without further purification.

$^1$H NMR (CDCl$_3$) d 8.20 (bs, 1H), 7.40–7.10 (m, 5H), 5.88 (s, 1H), 3.35 (dd, 1H), 2.80–2.50 (m, 4H), 2.25 (s, 3H).

Step 1-D:

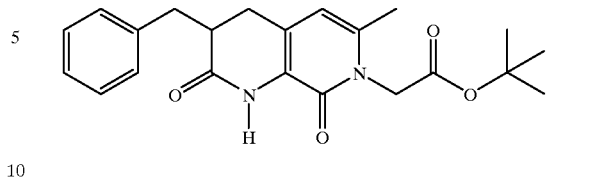
(1-4)

To a 23° C. solution of pyridone 1–3 (630 mg, 2.5 mmol) in 20 mL of DMF was added 812 mg (2.5 mmol) of Cs$_2$CO$_3$ and 0.37 mL (2.5 mmol) of tert-butyl bromoacetate. The reaction mixture was allowed to stir for 16 h before removal of the solvent in vacuo. The mixture was diluted with 100 mL of EtOAc and 25 mL water. The aqueous phase was discarded and the organic solution was washed with 20 mL of brine. Evaporation of the solvent and chromatography (1:1 EtOAc/Hexane) of the resulting oil left the alkylated pyridone as a white solid.

$^1$H NMR (CDCl$_3$) d 7.84 (bs, 1H), 7.33–7.17 (m, 5H), 5.87 (s, 1H), 4.79 (q, J=17.2 Hz, 2H), 3.36 (dd, J=4.1,13.5 Hz, 1H), 2.79 (m, 1H), 2.65 (m, 2H), 2.48 (m, 1H), 2.23 (s, 3H), 1.48 (s, 9H).

Step 1-E:

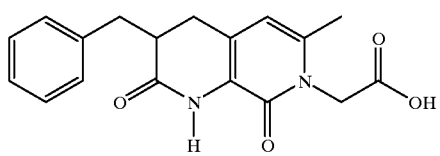
(1-5)

To a 0° C. solution of ester 1–4 (310 mg, 0.85 mmol) in 30 mL of DCM was added 8 mL of trifluoroacetic acid. The reaction mixture was allowed to stir to ambient temperature over 5 h before removal of the solvent in vacuo. The resulting solid was azeotroped with benzene, EtOAc then ether. This process yielded the desired carboxylic acid as a white solid.

$^1$H NMR (DMSO-d6) d 8.92 (bs, 1H), 7.35–7.10 (m, 5H), 6.04 (s, 1H), 4.75 (q, J=17.2 Hz, 2H), 3.16 (dd, J=4.2,13.7 Hz, 1H), 2.79 (m, 1H), 2.65–2.40 (m, 3H), 2.1 (s, 3H).

Step 1-F:

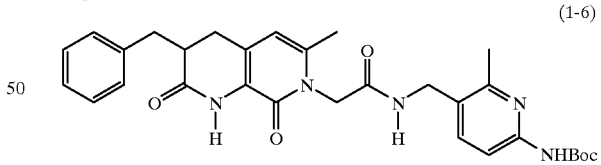
(1-6)

To a solution of acid 1–5 (240 mg, 0.90 mmol) and 237 mg (1.0 mmol) of 5-aminomethyl-2-boc-amino-6-methylpyridine in 5 mL of DMF was added 192 mg (1.0 mmol) of EDCI, 135 mg (1.0 mmol) of HOBT and 0.22 mL of N-methylmorpholine. The reaction mixture was allowed to stir for 16 h before removal of the solvent in vacuo. The mixture was diluted with 20 mL of EtOAc and 5 mL water. The aqueous phase was discarded and the organic solution was washed with 3×5 mL of water then 10 mL of brine. Evaporation of the solvent and chromatography (9:1 EtOAc/MeOH) afforded the desired product as a white solid.

$^1$H NMR (CDCl$_3$) d 8.47 (bs, 1H), 7.64 (d, J=9.0 Hz, 1H), 7.43–7.19 (m, 7H), 7.05 (bs, 1H), 5.95 (s, 1H), 4.75 (s, 2H), 4.37 (s, 2H), 3.32 (dd, J=4.1,13.5 Hz, 1H), 2.79–2.0 (m, 4H), 2.45 (s, 3H), 2.35 (s, 3H), 1.58 (s, 9H).

Step 1-G:

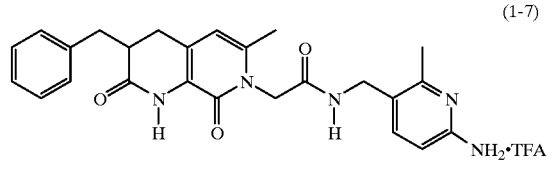
(1-7)

A solution of bicyclic substrate 1–6 (410 mg, 0.85 mmol) was dissolved in 12 mL of a 1:1 mixture of DCM and TFA. The reaction mixture was allowed to stir for 3 h before removal of the solvent in vacuo. The resulting solid was azeotroped with benzene, EtOAc then ether. This process yielded the desired compound as a white solid. Several 3 mg samples of the free base of this compound were each dissolved in 1 mL of MeOH and the enantiomers were separated on a Chiralcel OD column (250×4.6 mm; A=hexane w/0.1% diethylamine, B=EtOH, A:B=15/85; flow=7 mL/min).

$^1$H NMR (CD$_3$OD) d 7.84 (d, J=9.0 Hz, 1H), 7.40–7.20 (m, 5H), 6.79 (d, J=9.0 Hz, 1H), 6.18 (s, 1H), 4.80 (s, 2H), 4.27 (s, 2H), 3.16 (dd, J=4.1,13.5 Hz, 1H), 2.85–2.44 (m, 4H), 2.0 (s, 3H), 2.38 (s, 3H).

EXAMPLE 2

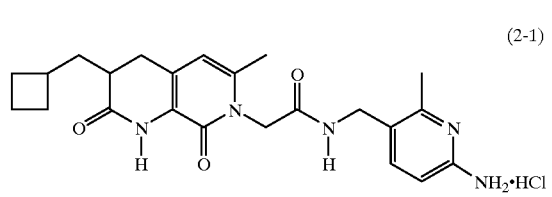
(2-1)

Compound 2–1 was prepared using the procedure outlined in example 1 but substituting trimethyl 2-cyclobutyl-2-phosphonopropionate (I-2) as the Emmon's reagent in step 1-A.

$^1$H NMR (CD$_3$OD) d 7.86 (d, J=9.0 Hz, 1H), 6.82 (d, J=9.0 Hz, 1H), 6.20 (s, 1H), 4.80 (s, 2H), 4.25 (s, 2H), 2.95 (dd, J=4.1,13.5 Hz, 1H), 2.60 (m, 1H), 2.59 (s, 3H), 2.48 (m, 2H), 2.38 (s, 3H), 2.20–1.60 (m, 8H).

EXAMPLE 3

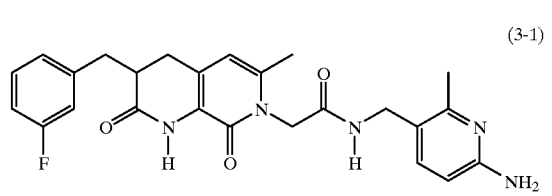
(3-1)

Compound 3-1 was prepared using the procedure outlined in example 1 but substituting trimethyl 2-(3-fluorobenzyl)-2-phosphonoacetate (I-6) as the Emmon's reagent in step 1-A. The free base of this compound was liberated by the action of ammonia in chloroform and the compound was chromatographed (9:1 CHCl$_3$ sat'd with NH$_3$/CH$_3$OH) to afford the final product.

$^1$H NMR (CD$_3$OD) d 7.40 (d, J=9.0 Hz, 1H), 7.35 (m, 2H), 7.00 (m, 2H), 6.42 (d, J=9.0 Hz, 1H), 6.15 (s, 1H), 4.80 (s, 2H), 4.25 (s, 2H), 3.25 (dd, J=4.1,13.5 Hz, 1H), 3.20 (m, 2H), 2.75 (m, 2H), 2.35 (s, 3H), 2.20 (s, 3H).

EXAMPLE 4

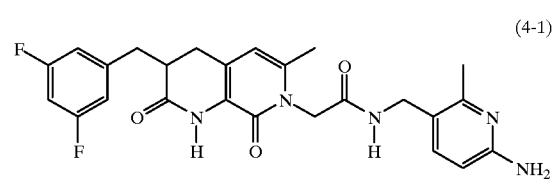
(4-1)

Compound (4-1) was prepared using the procedure outlined in example 1 but substituting trimethyl 2-(3,5-difluorobenzyl)-2-phosphonoacetate (I-8) as the Emmon's reagent in step 1-A. The free base of this compound was liberated by the action of ammonia in chloroform and the compound was chromatographed (9:1 CHCl$_3$ sat'd with NH$_3$/CH$_{30}$H) to afford the final product.

$^1$H NMR (CD$_3$OD) d 7.40 (d, J=9.0 Hz, 1H), 7.35 (m, 2H), 7.00 (m, 2H), 6.42 (d, J=9.0 Hz, 1H), 6.15 (s, 1H), 4.80 (s, 2H), 4.25 (s, 2H), 3.25 (dd, J=4.1,13.5 Hz, 1H), 3.20 (m, 2H), 2.75 (m, 2H), 2.35 (s, 3H), 2.20 (s, 3H).

EXAMPLE 5

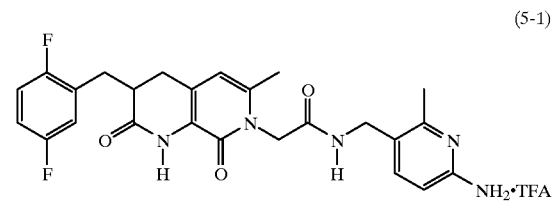
(5-1)

Compound (5-1) was prepared using the procedure outlined in example 1 but substituting trimethyl 2-(2,5-difluorobenzyl)-2-phosphonoacetate (I-7) as the Emmon's reagent in step 1-A $^1$H NMR (CD$_3$OD) d 7.80 (d, J=9.0 Hz, 1H), 7.2–6.9 (m, 3H), 6.82 (d, J=9.0 Hz, 1H), 6.05 (s, 1H), 4.80 (s, 2H), 4.35 (s, 2H), 3.25 (dd, J=4.1,13.5 Hz, 1H), 2.8–2.6 (m, 4H), 2.52 (s, 3H), 2.35 (s, 3H).

EXAMPLE 6

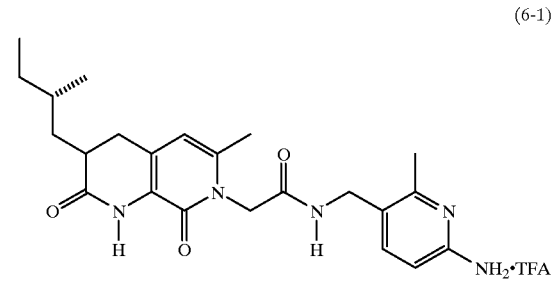
(6-1)

Compound (6-1) was prepared using the procedure outlined in example 1 but substituting trimethyl 4-(S)-methyl-2-phosphonohexenoate (I-6) as the Emmon's reagent in step 1-A $^1$H NMR (CD$_3$OD) d 7.86 (d, J=9.0 Hz, 1H), 6.82 (d, J=9.0 Hz, 1H), 6.11 (s, 1H), 4.80 (s, 2H), 4.25 (s, 2H), 2.99

(m, 1H), 2.64 (m, 2H), 2.55 (s, 3H), 2.30 (s, 3H), 1.75 (m, 1H), 1.55 (m, 2H), 1.40 (m, 2H), 1.20 (m, 2H), 0.90 (m, 6H).

EXAMPLE 7

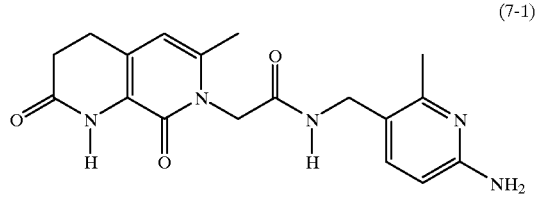

(7-1)

Compound 7-1 was prepared using the procedure outlined in example 1 but substituting commercially available trimethyl phosphonoacetate as the Emmon's reagent in step 1-A. The free base of this compound was liberated by the action of ammonia in chloroform and the compound was chromatographed (1:1 CHCl$_3$ sat'd with NH$_3$/CH$_3$OH) to afford the final product.

$^1$H NMR (CD$_3$OD) d 7.40 (d, J=9.0 Hz, 1H), 6.40 (d, J=9.0 Hz, 1H), 6.21 (s, 1H), 4.80 (s, 2H), 4.25 (s, 2H), 2.85 (t, J=7 Hz, 1H), 2.60 (t, J=7 Hz, 2H), 2.35 (s, 3H), 2.30 (s, 3H).

In vitro assay for determining proteinase inhibition

Assays of human a-thrombin and human trypsin were performed at 25° C. in 0.05 M TRIS buffer pH 7.4, 0.15 M NaCl, 0.1% PEG. Trypsin assays also contained 1 mM CaCl$_2$.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human a-thrombin (Km=125 $\mu$M) and human trypsin (Km=59 $\mu$M). p-Nitroanilide substrate concentration was determined from measurements of absorbance at 342 nm using an extinction coefficient of 8270 cm-$^{-1}$M-$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) (K$_m$=27 $\mu$M) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethylcoumarin produced upon complete hydrolysis of an aliquot of the stock solution by thrombin.

Activity assays were performed by diluting a stock solution of substrate at least tenfold to a final concentration ≦0.5 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in equation 1.

$$V_o/V_i = 1 + [I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

In Vivo Studies To Measure Thrombotic Occlusions

Studies of 3-(2-Phenylethylamino)-6-methyl-1-(2-amino-6-methyl-5-methylenecarboxamidomethylpyridinyl)-2-pyridinone using the following rat ferric chloride assay substantially as described in *Thrombosis Research*, No. 60, page 269(1990) by Kurtz et al were used to determine in vivo activity of the thrombin inhibitors of the invention. Male Sprague-Dawley rats (body weights 200–350 grams) were anesthetized with dial-urethane solution (0.1 ml/100 gm body weight i.p.), and a lateral tail vein was cannulated with a 23 gauge needle connected to a 12 inch length of PE50 tubing. The tubing was attached to a 3-way valve by a tubing adapter. Saline (control) or test compound, as appropriate, was administered via the tail vein catheter. A tracheostomy was performed with a 0.75 inch length of PE205 tubing. The right carotid artery is exposed and a 1.3 mm diameter Doppler flow probe was placed on the vessel. Body temperature was maintained at 37° C. using a heat lamp.

6 rats were randomized to continuous intravenous infusions of saline or test compound administered via the tail vein. Test compound was administered at a rate of 10 $\mu$g/kg/min. Treatment infusions were initiated 60 min before the placement of a 3 mm square piece of Whatman No. 1 filter paper saturated with 35% FeCl$_3$ onto the exposed carotid artery distal to the flow probe. Treatment infusions were continued for an additional 90 minutes after the application of FeCl$_3$ (total infusion duration 150 minutes) if thrombotic occlusions did not occur, or were terminated 30 minutes after thrombotic occlusion of the vessel. Time to occlusion was defined as the time from application of FeCl$_3$ to thrombotic occlusion of the vessel. At the termination of the study (90 minutes after application of FeCl$_3$ in animals which did not occlude, or at 30 minutes after thrombotic occlusion), 3 ml blood samples were drawn by cardiac puncture into 0.3 ml of 3.8% sodium citrate.

EXAMPLE 8

Tablet Preparation

Tablets containing 25.0, 50.0, and 100.0 mg., respectively, of compound 1-7 ("active compound") are prepared as illustrated below:

TABLE FOR DOSES CONTAINING FROM 25–100 MG OF THE ACTIVE COMPOUND

|  | Amount-mg | | |
| --- | --- | --- | --- |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 9

Tablet Preparation

Exemplary compositions of compound 1-7 tablets are shown below:

| Component | 0.25 mg | 2 mg | 10 mg | 50 mg |
|---|---|---|---|---|
| compound 1-7 | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet preparation via direct compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet preparation via dry granulation

Alternatively, a dry powder blend is compacted under modest forces and remilled to afford granules of specified particle size. The granules are then mixed with magnesium stearate and tabletted as stated above.

EXAMPLE 10

Intravenous Formulations

Intravenous formulations of compound 1-7 were prepared according to general intravenous formulation procedures.

| Component | Estimated range |
|---|---|
| Compound 1-7 | 0.12–0.61 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Exemplary compositions A-C are as follows:

| Component | A | B | C |
|---|---|---|---|
| Compound 1-7 | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection q.s. | 1.0 mL q.s. | 1.0 mL q.s. | 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound having the following structure:

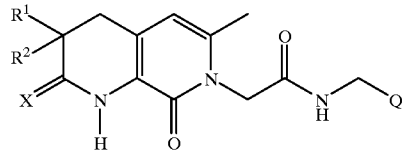

wherein
X is O or H$_2$;
R$^1$ and R$^2$ are independently selected from the group consisting of
hydrogen,
C$_{1-6}$ alkyl-,
C$_{2-6}$ alkenyl,
C$_{2-6}$ alkynyl,
C$_{3-8}$ cycloalkyl-
C$_{3-8}$cycloalkyl C$_{1-6}$alkyl-,
di(C$_{3-8}$cycloalkyl) C$_{1-6}$alkyl-,
aryl,
aryl C$_{1-6}$ alkyl-,
di(aryl) C$_{1-6}$ alkyl-,
wherein aryl is an unsaturated 6-carbon ring, either unsubstituted or substituted with —OH, —NH$_2$, C$_{1-6}$alkyl, C$_{3-8}$cycloalkyl, or halogen;
and
Q is

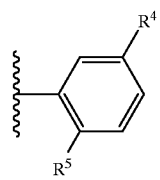

wherein R$^4$ and R$^5$ are independently selected from the group consisting of
hydrogen,
C$_{1-4}$ alkyl,
C$_{2-4}$ alkenyl,
C$_{2-4}$ alkynyl,
C$_{1-4}$ alkoxy,
halogen,
—COOH,
—OH,
—COOR$^7$, where R$^7$ is C$_{1-4}$alkyl,
—CONR$^8$R$^9$, where R$^8$ and R$^9$ are independently hydrogen or C$_{1-4}$alkyl,
—OCH$_2$CO$_2$H,
—OCH$_2$CO$_2$CH$_3$, —OCH$_2$CO$_2$(CH$_2$)$_{1-3}$CH$_3$,
—O(CH$_2$)$_{1-3}$C(O)NR$^{10}$R$^{11}$, wherein R$^{10}$ and R$^{11}$ are independently hydrogen, C$_{1-4}$alkyl, C$_{3-7}$ cycloalkyl, or —CH$_2$CF$_3$,
—(CH$_2$)$_{1-4}$OH,
—NHC(O)CH$_3$,
—NHC(O)CF$_3$,
—NHSO$_2$CH$_3$,
—SO$_2$NH$_2$;

or Q is

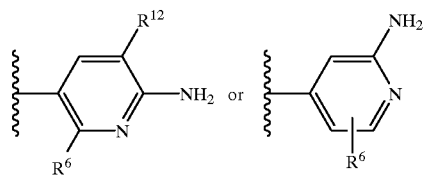

wherein R$^6$ and R$^{12}$, same or different, are
hydrogen,
C$_{1-6}$ alkyl-,
C$_{2-6}$ alkenyl-,
C$_{2-6}$ alkynyl,
C$_{3-8}$ cycloalkyl-,
aryl,
aryl C$_{1-6}$alkyl-
wherein aryl is an unsaturated 6-carbon ring either unsubstituted or substituted with —OH, —NH$_2$, C$_{1-6}$alkyl, C$_{3-8}$ cycloalkyl, or halogen.
or a pharmaceutically acceptable salt thereof.

2. A compound of claim 1 wherein

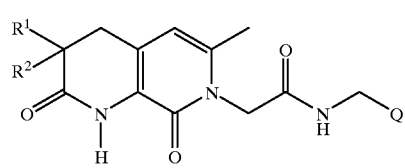

wherein
R$^1$ and R$^2$ are independently selected from the group consisting of:
hydrogen,
C$_{1-6}$alkyl,
C$_{3-8}$cycloalkylC$_{1-6}$alkyl-,
di(C$_{3-8}$cycloalkyl)Cl 6alkyl-,
aryl C$_{1-6}$alkyl-,
di(aryl) Cl-6alkyl-,
wherein aryl is unsubstituted, monosubstituted or disubstituted with halogen,
and
Q is

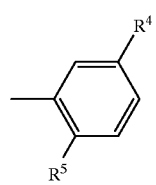

wherein R$^4$ and R$^5$ are independently selected from the group consisting of
hydrogen,
halogen, or
—OCH$_2$C(O)NHR$^{11}$, wherein R$^{11}$ is C$_{1-4}$ alkyl, or Q is

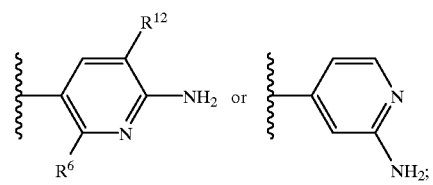

where R$^6$ and R$^{12}$, same or different, are hydrogen or —CH$_3$,
or a pharmaceutically acceptable salt thereof.

3. A compound of claim 2 wherein

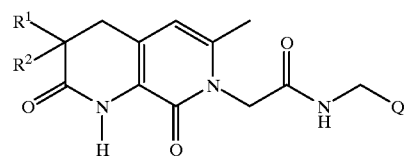

wherein
R$^1$ is hydrogen,

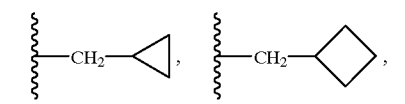

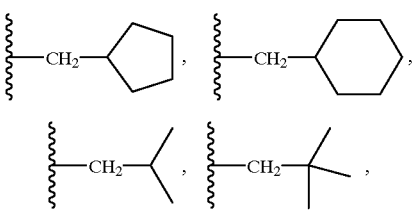

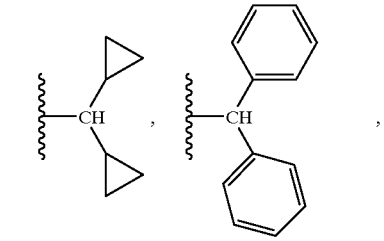

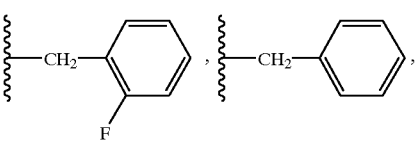

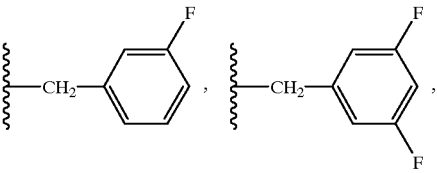

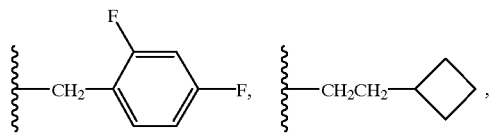

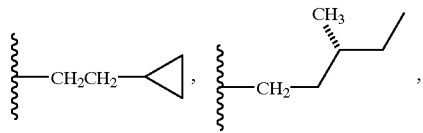

$R^2$ is hydrogen, $CH_3$, $C_{1-6}$ alkyl, and aryl$C_{1-6}$alkyl; and Q is

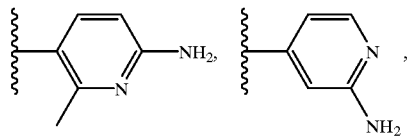

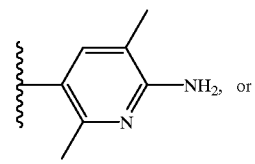

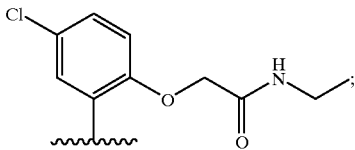

or a pharmaceutically acceptable salt thereof.

4. A compound of claim 3 wherein

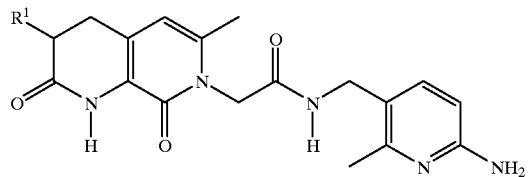

wherein
$R^1$ is hydrogen,

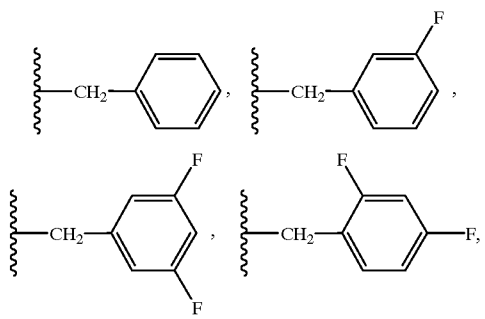

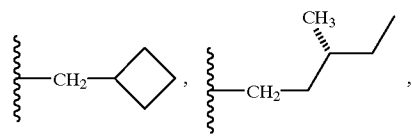

or a pharmaceutically acceptable salt thereof.

5. A compound of claim 4 selected from the group consisting of

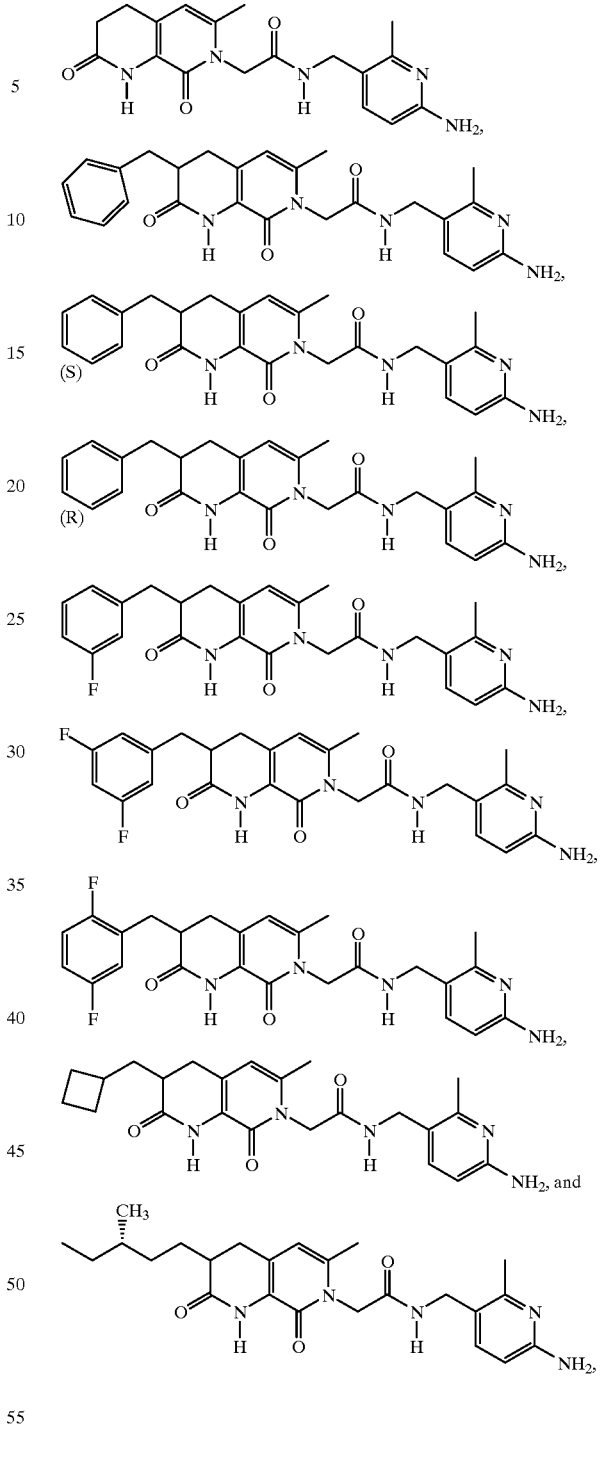

or a pharmaceutically acceptable salt thereof.

6. A composition comprising an effective amount of a compound of claim 1 and a pharmaceutically acceptable carrier.

* * * * *